(12) United States Patent
Krolik et al.

(10) Patent No.: US 8,123,777 B2
(45) Date of Patent: Feb. 28, 2012

(54) APPARATUS AND METHODS FOR ASPIRATING EMBOLI

(75) Inventors: Jeffrey Krolik, Campbell, CA (US); Amr Salahieh, Saratoga, CA (US)

(73) Assignee: Incept, LLC, San Mateo, CA (US)

( * ) Notice: Subject to any disclaimer, the term of this patent is extended or adjusted under 35 U.S.C. 154(b) by 1048 days.

(21) Appl. No.: 11/241,029

(22) Filed: Sep. 30, 2005

(65) Prior Publication Data

US 2006/0025806 A1    Feb. 2, 2006

Related U.S. Application Data

(63) Continuation of application No. 09/912,862, filed on Jul. 24, 2001, now abandoned.

(51) Int. Cl.
*A61M 29/00* (2006.01)

(52) U.S. Cl. .................................... 606/200

(58) Field of Classification Search ............... 606/159, 606/170, 194, 200, 192; 604/96, 7, 22, 101, 604/19, 171, 264, 280
See application file for complete search history.

(56) References Cited

U.S. PATENT DOCUMENTS

| | | | |
|---|---|---|---|
| 3,472,230 A | 10/1969 | Fogarty | 128/328 |
| 3,592,186 A | 7/1971 | Oster | 128/2 R |
| 3,683,904 A | 8/1972 | Forster | 128/127 |
| 3,889,657 A | 6/1975 | Baumgarten | 128/2 |
| 3,952,747 A | 4/1976 | Kimmell, Jr. | 128/303 R |
| 3,965,901 A * | 6/1976 | Penny et al. | 604/119 |
| 3,996,938 A | 12/1976 | Clark, III | 128/348 |
| 4,046,150 A | 9/1977 | Schwartz et al. | 128/328 |
| 4,425,908 A | 1/1984 | Simon | 128/1 |
| 4,447,227 A | 5/1984 | Kotsanis | 604/95 |
| 4,580,568 A | 4/1986 | Gianturco | 128/345 |
| 4,590,938 A | 5/1986 | Segura et al. | 128/328 |
| 4,619,246 A | 10/1986 | Molgaard-Nielsen et al. | 128/1 |
| 4,631,052 A | 12/1986 | Kensey | 604/22 |
| 4,643,184 A | 2/1987 | Mobin-Uddin | 128/303 |
| 4,650,466 A | 3/1987 | Luther | 604/95 |
| 4,662,885 A | 5/1987 | DiPisa, Jr. | 623/12 |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner* — Tuan Nguyen (74) *Attorney, Agent, or Firm* — Seager, Tufte & Wickhem, LLC (57) ABSTRACT

Apparatus and methods for aspirating emboli from a vascular filter or stent within a patient's circulatory system are provided. A filter sac of the vascular filter permits blood flow and captures emboli from the flow. The aspiration device removes emboli from within or proximal to the vascular filter or stent to reduce the risk to the ischemia during retrieval of the vascular filter and during a treatment procedure. Retrieval of the vascular filter may be accomplished using either the aspiration catheter or a separate retrieval catheter.

14 Claims, 8 Drawing Sheets

U.S. PATENT DOCUMENTS

| | | | |
|---|---|---|---|
| 4,705,517 A | 11/1987 | DiPisa, Jr. | 623/12 |
| 4,706,671 A | 11/1987 | Weinrib | 128/348.1 |
| 4,723,549 A | 2/1988 | Wholey et al. | 128/344 |
| 4,728,319 A | 3/1988 | Masch | 604/22 |
| 4,733,665 A | 3/1988 | Palmaz | 128/343 |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | 128/344 |
| 4,794,931 A | 1/1989 | Yock | 128/660.03 |
| 4,800,882 A | 1/1989 | Gianturco | 128/343 |
| 4,807,626 A | 2/1989 | McGirr | 128/328 |
| 4,842,579 A | 6/1989 | Shiber | 606/22 |
| 4,857,045 A | 8/1989 | Rydell | 604/22 |
| 4,857,046 A | 8/1989 | Stevens et al. | 604/22 |
| 4,867,157 A | 9/1989 | McGurk-Burleson et al. | 128/305 |
| 4,873,978 A | 10/1989 | Ginsburg | 128/345 |
| 4,886,061 A | 12/1989 | Fischell et al. | |
| 4,898,575 A | 2/1990 | Fischell et al. | 604/22 |
| 4,907,336 A | 3/1990 | Gianturco | 29/515 |
| 4,921,478 A | 5/1990 | Solano et al. | 604/53 |
| 4,921,484 A | 5/1990 | Hillstead | 604/104 |
| 4,926,858 A | 5/1990 | Gifford, III et al. | 606/159 |
| 4,950,277 A | 8/1990 | Farr | 606/159 |
| 4,955,895 A | 9/1990 | Sugiyama et al. | 606/194 |
| 4,957,482 A | 9/1990 | Shiber | 604/22 |
| 4,969,891 A | 11/1990 | Gewertz | 606/200 |
| 4,979,951 A | 12/1990 | Simpson | 606/159 |
| 4,986,807 A | 1/1991 | Farr | 604/22 |
| 4,998,539 A | 3/1991 | Delsanti | 128/898 |
| 5,002,560 A | 3/1991 | Machold et al. | 606/198 |
| RE33,569 E | 4/1991 | Gifford, III et al. | 606/159 |
| 5,007,896 A | 4/1991 | Shiber | 604/22 |
| 5,007,917 A | 4/1991 | Evans | 606/170 |
| 5,011,488 A | 4/1991 | Ginsburg | 606/159 |
| 5,019,088 A | 5/1991 | Farr | 606/159 |
| 5,041,126 A | 8/1991 | Gianturco | 606/195 |
| 5,053,008 A | 10/1991 | Bajaj | 604/104 |
| 5,053,044 A | 10/1991 | Mueller et al. | 606/159 |
| 5,071,407 A | 12/1991 | Termin et al. | 604/104 |
| 5,071,425 A | 12/1991 | Gifford, III et al. | 606/159 |
| 5,085,662 A | 2/1992 | Willard | 606/159 |
| 5,087,265 A | 2/1992 | Summers | 606/159 |
| 5,100,423 A | 3/1992 | Fearnot | 606/15 |
| 5,100,424 A | 3/1992 | Jang et al. | 606/159 |
| 5,100,425 A | 3/1992 | Fischell et al. | 606/159 |
| 5,102,415 A | 4/1992 | Guenther et al. | 606/159 |
| 5,104,399 A | 4/1992 | Lazarus | 623/1 |
| 5,108,419 A | 4/1992 | Reger et al. | 606/200 |
| 5,133,733 A | 7/1992 | Rasmussen et al. | 606/200 |
| 5,135,531 A | 8/1992 | Shiber | 606/159 |
| 5,152,771 A | 10/1992 | Sabbaghian et al. | 606/159 |
| 5,152,777 A | 10/1992 | Goldberg et al. | 606/200 |
| 5,160,342 A | 11/1992 | Reger et al. | 606/200 |
| 5,171,233 A | 12/1992 | Amplatz et al. | 604/281 |
| 5,190,546 A | 3/1993 | Jervis | 606/78 |
| 5,192,286 A | 3/1993 | Phan et al. | |
| 5,195,955 A | 3/1993 | Don Michael | 604/22 |
| 5,224,953 A | 7/1993 | Morgentaler | 606/192 |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,318,576 A | 6/1994 | Plassche, Jr. et al. | 606/159 |
| 5,324,304 A | 6/1994 | Rasmussen | |
| 5,329,942 A | 7/1994 | Gunther et al. | 128/898 |
| 5,330,484 A | 7/1994 | Gunther et al. | 606/128 |
| 5,330,500 A | 7/1994 | Song | 606/198 |
| 5,350,398 A | 9/1994 | Pavcnik et al. | 606/200 |
| 5,354,310 A | 10/1994 | Garnic et al. | 606/198 |
| 5,356,423 A | 10/1994 | Tihon et al. | 606/194 |
| 5,366,464 A | 11/1994 | Belknap | 606/159 |
| 5,366,473 A | 11/1994 | Winston et al. | 606/198 |
| 5,370,657 A | 12/1994 | Irie | 606/200 |
| 5,370,683 A | 12/1994 | Fontaine | 623/1 |
| 5,376,100 A | 12/1994 | Lefebvre | 606/180 |
| 5,383,887 A | 1/1995 | Nadal | 606/200 |
| 5,383,892 A | 1/1995 | Cardon et al. | 606/198 |
| 5,383,926 A | 1/1995 | Lock et al. | 623/1 |
| 5,387,235 A | 2/1995 | Chuter | 623/1 |
| 5,395,349 A | 3/1995 | Quiachon et al. | 604/248 |
| 5,397,345 A | 3/1995 | Lazarus | 623/1 |
| 5,405,377 A | 4/1995 | Cragg | 623/1 |
| 5,409,454 A | 4/1995 | Fischell et al. | 604/22 |
| 5,415,630 A | 5/1995 | Gory et al. | 604/53 |
| 5,419,774 A | 5/1995 | Willard et al. | 604/22 |
| 5,421,832 A | 6/1995 | Lefebvre | 604/53 |
| 5,423,742 A | 6/1995 | Theron | 604/28 |
| 5,423,885 A | 6/1995 | Williams | 623/1 |
| 5,425,765 A | 6/1995 | Tiefenbrun et al. | 623/12 |
| 5,443,498 A | 8/1995 | Fontaine | 623/1 |
| 5,449,372 A | 9/1995 | Schmaltz et al. | 606/198 |
| 5,456,667 A | 10/1995 | Ham et al. | 604/107 |
| 5,462,529 A | 10/1995 | Simpson et al. | 604/101 |
| 5,476,104 A | 12/1995 | Sheahon | 128/757 |
| 5,484,418 A | 1/1996 | Quiachon et al. | 604/167 |
| 5,507,767 A | 4/1996 | Maeda et al. | 606/198 |
| 5,512,044 A | 4/1996 | Duer | 604/22 |
| 5,527,354 A | 6/1996 | Fontaine et al. | 623/1 |
| 5,536,242 A | 7/1996 | Willard et al. | 604/30 |
| 5,540,707 A | 7/1996 | Ressemann et al. | 606/159 |
| 5,549,626 A | 8/1996 | Miller et al. | 606/200 |
| 5,562,724 A | 10/1996 | Vowerk et al. | 623/1 |
| 5,569,274 A | 10/1996 | Rapacki et al. | 606/158 |
| 5,569,275 A | 10/1996 | Kotula et al. | 606/159 |
| 5,634,897 A | 6/1997 | Dance et al. | 604/35 |
| 5,658,296 A | 8/1997 | Bates et al. | 606/127 |
| 5,662,671 A | 9/1997 | Barbut et al. | 606/170 |
| 5,669,933 A | 9/1997 | Simon et al. | 600/200 |
| 5,695,519 A | 12/1997 | Summers et al. | 606/200 |
| 5,709,704 A | 1/1998 | Nott et al. | 606/200 |
| 5,720,764 A | 2/1998 | Naderlinger | 606/200 |
| 5,728,066 A | 3/1998 | Daneshvar | 604/96 |
| 5,746,758 A | 5/1998 | Nordgren et al. | 606/159 |
| 5,749,848 A | 5/1998 | Jang et al. | 604/53 |
| 5,749,858 A | 5/1998 | Cramer | |
| 5,769,816 A | 6/1998 | Barbut et al. | 604/96 |
| 5,779,716 A | 7/1998 | Cano et al. | 606/114 |
| 5,792,300 A | 8/1998 | Inderbitzen et al. | 156/244.13 |
| 5,795,322 A | 8/1998 | Boudewijn | 604/22 |
| 5,797,952 A | 8/1998 | Klein | 606/198 |
| 5,800,457 A | 9/1998 | Gelbfish | 606/200 |
| 5,800,525 A | 9/1998 | Bachinski et al. | 623/1 |
| 5,807,398 A | 9/1998 | Shaknovich | |
| 5,810,874 A | 9/1998 | Lefebvre | 606/200 |
| 5,814,064 A | 9/1998 | Daniel et al. | 606/200 |
| 5,817,102 A | 10/1998 | Johnson et al. | 606/108 |
| 5,827,229 A | 10/1998 | Auth et al. | |
| 5,827,324 A | 10/1998 | Cassell et al. | 606/200 |
| 5,833,644 A | 11/1998 | Zadno-Azizi et al. | 604/52 |
| 5,833,650 A | 11/1998 | Imran | 604/53 |
| 5,846,260 A | 12/1998 | Maahs | 606/200 |
| 5,848,964 A | 12/1998 | Samuels | 600/200 |
| 5,876,367 A | 3/1999 | Kaganov et al. | 604/8 |
| 5,893,867 A | 4/1999 | Bagaoisan et al. | 606/198 |
| 5,893,869 A | 4/1999 | Barnhart et al. | |
| 5,895,399 A | 4/1999 | Barbut et al. | 606/159 |
| 5,902,263 A | 5/1999 | Patterson et al. | 604/22 |
| 5,906,618 A | 5/1999 | Larson, III | 606/108 |
| 5,908,435 A | 6/1999 | Samuels | 606/200 |
| 5,910,154 A | 6/1999 | Tsugita et al. | 606/200 |
| 5,911,734 A | 6/1999 | Tsugita et al. | 606/200 |
| 5,916,193 A | 6/1999 | Stevens et al. | 604/53 |
| 5,925,016 A | 7/1999 | Chornenky et al. | 604/96 |
| 5,925,060 A | 7/1999 | Forber | 606/191 |
| 5,925,062 A | 7/1999 | Purdy | 606/200 |
| 5,925,063 A | 7/1999 | Khosravi | 606/200 |
| 5,928,203 A | 7/1999 | Davey et al. | 604/247 |
| 5,928,218 A | 7/1999 | Gelbfish | 604/540 |
| 5,934,284 A | 8/1999 | Plaia et al. | 128/898 |
| 5,935,139 A | 8/1999 | Bates | 606/159 |
| 5,938,645 A | 8/1999 | Gordon | 604/264 |
| 5,941,869 A | 8/1999 | Patterson et al. | 604/508 |
| 5,941,896 A | 8/1999 | Kerr | 606/200 |
| 5,947,995 A | 9/1999 | Samuels | 606/200 |
| 5,951,585 A | 9/1999 | Cathcart et al. | 606/198 |
| 5,954,745 A | 9/1999 | Gertler et al. | 606/200 |

| Patent No. | | Date | Inventor | Class |
|---|---|---|---|---|
| 5,976,172 | A | 11/1999 | Homsma et al. | 606/200 |
| 5,989,210 | A | 11/1999 | Morris et al. | 604/22 |
| 5,989,271 | A | 11/1999 | Bonnette et al. | 606/159 |
| 5,989,281 | A | 11/1999 | Barbut et al. | 606/200 |
| 5,993,469 | A | 11/1999 | McKenzie et al. | 606/159 |
| 5,997,557 | A | 12/1999 | Barbut et al. | 606/159 |
| 6,001,118 | A | 12/1999 | Daniel et al. | 606/200 |
| 6,007,557 | A | 12/1999 | Ambrisco et al. | 606/200 |
| 6,010,522 | A | 1/2000 | Barbut et al. | 606/200 |
| 6,013,085 | A | 1/2000 | Howard | 606/108 |
| 6,027,520 | A | 2/2000 | Tsugita et al. | 606/200 |
| 6,051,014 | A | 4/2000 | Jang | 606/200 |
| 6,053,932 | A | 4/2000 | Daniel et al. | 606/200 |
| 6,059,814 | A | 5/2000 | Ladd | 606/200 |
| 6,066,149 | A | 5/2000 | Samson et al. | |
| 6,066,158 | A | 5/2000 | Engelson et al. | |
| 6,068,645 | A | 5/2000 | Tu | 606/200 |
| 6,086,605 | A | 7/2000 | Barbut et al. | 606/200 |
| 6,129,739 | A | 10/2000 | Khosravi | 606/200 |
| 6,135,991 | A | 10/2000 | Muni et al. | |
| 6,142,987 | A | 11/2000 | Tsugita | 604/500 |
| 6,152,946 | A | 11/2000 | Broome et al. | 606/200 |
| 6,152,947 | A | 11/2000 | Ambrisco et al. | |
| 6,165,200 | A | 12/2000 | Tsugita et al. | 606/200 |
| 6,168,579 | B1 | 1/2001 | Tsugita | 604/96.01 |
| 6,171,327 | B1 | 1/2001 | Daniel et al. | 606/200 |
| 6,179,851 | B1 | 1/2001 | Barbut et al. | 606/159 |
| 6,179,859 | B1 | 1/2001 | Bates et al. | 606/200 |
| 6,179,861 | B1 | 1/2001 | Khosravi et al. | 606/200 |
| 6,203,561 | B1 | 3/2001 | Ramee et al. | 606/200 |
| 6,206,868 | B1 | 3/2001 | Parodi | |
| 6,214,026 | B1 | 4/2001 | Lepak et al. | 606/200 |
| 6,221,006 | B1 | 4/2001 | Dubrul et al. | |
| 6,277,139 | B1 | 8/2001 | Levinson et al. | |
| 6,371,970 | B1 | 4/2002 | Khosravi et al. | |
| 6,499,487 | B1 * | 12/2002 | McKenzie et al. | 128/898 |
| 6,544,279 | B1 | 4/2003 | Hopkins et al. | |
| 6,565,591 | B2 | 5/2003 | Brady et al. | |
| 6,596,011 | B2 * | 7/2003 | Johnson et al. | 606/200 |
| 6,605,102 | B1 | 8/2003 | Mazzocchi et al. | |
| 6,616,682 | B2 | 9/2003 | Joergensen et al. | |
| 6,620,182 | B1 | 9/2003 | Khosravi et al. | |
| 6,712,835 | B2 | 3/2004 | Mazzocchi et al. | |
| 6,723,085 | B2 | 4/2004 | Jang et al. | |
| 6,849,068 | B1 * | 2/2005 | Bagaoisan et al. | 604/523 |
| 2002/0022858 | A1 | 2/2002 | Demond et al. | |
| 2003/0023263 | A1 | 1/2003 | Krolik et al. | |
| 2003/0078614 | A1 | 4/2003 | Salahieh et al. | |
| 2004/0019310 | A1 | 1/2004 | Hogendijk | |
| 2005/0004594 | A1 | 1/2005 | Nool et al. | |
| 2005/0033347 | A1 | 2/2005 | Rauker et al. | |
| 2005/0277976 | A1 | 12/2005 | Galdonik et al. | |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 92/03097 | 3/1992 |
| WO | WO 94/14389 | 7/1994 |
| WO | WO 94/24946 | 11/1994 |
| WO | 96/01591 A1 | 1/1996 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 01/10343 A1 | 2/2002 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604. (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," l*American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with Systemic embolization: A new finding seen by transesophageal echocardiography," *American Heart Journal* 120(3):658-660 (Sep. 1990).

Waksman et al., "Distal Embolization is Common After Directional Heart Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

APPARATUS AND METHODS FOR ASPIRATING EMBOLI

This application is a continuation application of U.S. application Ser. No. 09/912,862 as filed, Jul. 24, 2001 now abandoned.

FIELD OF THE INVENTION

The present invention relates to apparatus and methods for aspirating emboli. More particularly, the present invention provides apparatus useful for aspirating emboli from a vascular device such as a vascular filter used to prevent embolization associated with diagnostic or therapeutic interventional procedures, thrombectomy and embolectomy.

BACKGROUND OF THE INVENTION

Percutaneous interventional procedures to treat occlusive vascular disease, such as angioplasty, atherectomy, and stenting, often dislodge material from the vessel walls. This dislodged material, known as emboli, enters the bloodstream and may be large enough to occlude smaller downstream vessels, potentially blocking blood flow to tissue. The resulting ischemia poses a serious threat to the health or life of a patient if the blockage occurs in critical tissue, such as the heart, lungs, or brain.

The deployment of stents and stent-grafts to treat vascular disease, such as aneurysms, involves the introduction of foreign objects into the bloodstream, and also may result in the formation of clots or release of emboli. Such particulate matter, if released into the bloodstream, also may cause infarction or stroke.

Numerous blood filters have been designed to capture material liberated from vessel walls during the treatment of vascular disease. Such treatment procedures, such as angioplasty, typically involve transluminally inserting an interventional device, such as an angioplasty catheter, to the treatment site along a guidewire. During a typical interventional angioplasty treatment procedure, the balloon of the angioplasty catheter is inflated within the vessel at least once but often more than once. First a pre-dilatation angioplasty catheter is inflated against the vessel to pre-dilate it. Next a stent delivery angioplasty catheter is inflated to deploy the stent. Finally a post-dilation angioplasty catheter is inflated to properly seat the stent against the vessel. Each of the inflations and manipulations of the interventional devices often liberate emboli from the vessel walls. The emboli enters the bloodstream and flows into a vascular filter, where it remains for the duration of the treatment procedure.

Is has been postulated that a vascular filter may become occluded with emboli during a transluminal diagnostic or therapeutic procedure, thus occluding flow of blood through the filter. Additional emboli, generated proximal to the vascular filter by the angioplasty catheter, may then be unable to flow downstream and into the vascular filter. When the vascular filter is collapsed for retrieval, the restored flow of blood through the vessel may carry those additional emboli downstream past the collapsed filter, potentially jeopardizing the patient's health.

An additional disadvantage postulated to occur when retrieving an emboli-ladened vascular filter is that the vascular filter may become entangled with a stent disposed within the patient's vessel. If, for example, a stent has been deployed, the vascular filter may inadvertently engage a stent strut, preventing further advancement of the vascular filter within the vessel, or even possibly causing vessel dissection.

Also, emboli may temporarily adhere to stents disposed within a patient's vessel. When blood flow is subsequently restored, the emboli may re-enter the bloodstream and cause infarction or stroke.

In view of the foregoing, it would be desirable to provide improved apparatus and methods for aspirating emboli from a blood vessel in which a vascular filter is used in conjunction with a transluminal diagnostic or therapeutic procedure and/or in which a stent is deployed.

SUMMARY OF THE INVENTION

The present invention pertains to apparatus and methods for aspirating emboli from a blood vessel in which a vascular filter is used in conjunction with a transluminal diagnostic or therapeutic procedure and/or in which a stent is deployed. The risk associated with retrieving a vascular filter from a patient's vessel can be decreased by using an aspiration device that aspirates emboli from a blood vessel in which a vascular filter and/or a stent is placed.

The aspiration recovery devices of the present invention are intended to remove emboli immediately adjacent to or contained within a filter sac of a vascular filter. Additionally, the aspiration device may be used to retrieve the vascular filter. Two families of aspiration recovery devices are provided: a single catheter type and telescoping dual catheter type. The single catheter type device uses one catheter both to aspirate emboli and retrieve a vascular filter. The telescoping dual catheter type device uses two catheters, with one catheter disposed inside the other, so that the inner catheter is used to aspirate emboli from a vascular filter and the outer catheter is used to retrieve the vascular filter.

Both the single catheter and the telescoping dual catheter types of aspiration recovery devices may be over-the-wire devices or rapid exchange devices. Aspiration through the catheters may be accomplished using a syringe coupled to the catheter via a hemostatic valve, wherein retracting the plunger of the syringe aspirates and amount of blood from the patient in a range of about 10 ml to 50 ml. Alternatively, a vacuum hook-up, such as a standard suction port available in a hospital operating room, may be used.

Both rapid exchange and over-the-wire aspiration recovery devices of the present invention may be used to aspirate emboli from within or proximal to a vascular filter liberated from a patient's vessel wall by an interventional device. Devices constructed in accordance with the present invention also may be used to aspirate emboli from the filter sac of a vascular filter during a procedure. Additionally, the present invention may be used to aspirate emboli from around a stent placed in a patient's vessel.

DETAILED DESCRIPTION OF THE INVENTION

The present invention is directed to apparatus and methods for aspirating emboli from a blood vessel in which a vascular filter and/or a stent is used and decreasing the risk associated with retrieving a vascular filter from a patient's vessel.

A number of vascular filters are known for providing distal protection against embolization in conjunction with a transluminal diagnostic or therapeutic procedure, such as angioplasty. These filters generally are deployed distal to a vascular lesion prior to undertaking a diagnostic or therapeutic procedure, and are designed to filter emboli liberated during the procedure from the patient's blood. A brief description of a number of these filters is provided as context for advantages achievable using the apparatus of the present invention.

Figure 1:
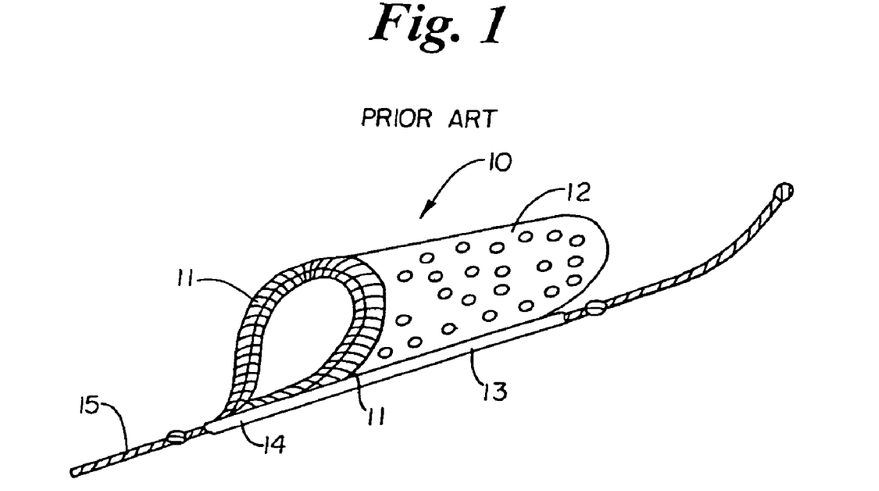
FIG. 1 is a perspective view of a first previously known vascular filter suitable for use with the apparatus of the present invention.

FIG. 1 shows vascular filter 10 described in U.S. Pat. No. 6,129,739 to Khosravi et al., which is incorporated herein in its entirety. Vascular filter 10 includes articulated support hoop 11 carrying blood-permeable element 12. Support hoop 11 is attached to tube 13 at point 14, and permits guidewire 15 to be rotated independently of support hoop 11. Blood-permeable element 12 filters emboli and other undesirable material from blood passing through the filter, while permitting blood cells to pass freely therethrough. When an interventional procedure, e.g., angioplasty or stenting, is completed, vascular filter 10 is retrieved by partially withdrawing support hoop 11 into the lumen of the interventional device (e.g., angioplasty catheter), and removing the catheter and vascular filter.

Figure 2:
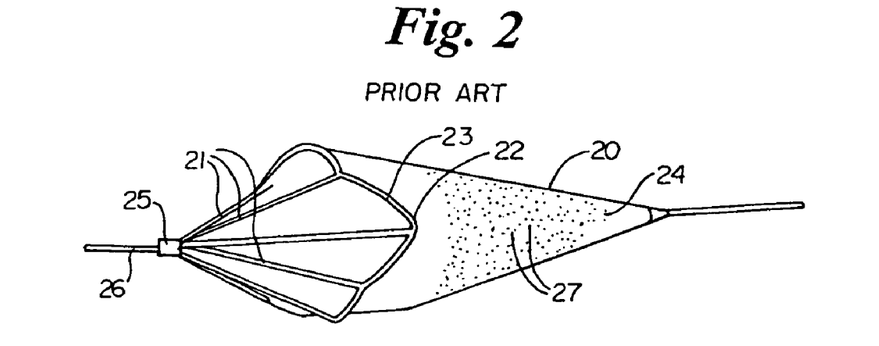
FIG. 2 is a perspective view of another previously known vascular filter suitable for use with the apparatus of the present invention.

FIG. 2 depicts another type of vascular filter suitable for use with the methods and apparatus of the present invention, and is described in U.S. Pat. No. 6,152,946 to Broome et al., which is incorporated herein by reference. Vascular filter 20 includes a plurality of longitudinally-extending ribs 21 forming frame 22 that supports mouth 23. Cone-shaped filter 24 is coupled to mouth 23. Ribs 21 are coupled to collar 25, which is displaced distally along guidewire 26 to expand and deploy frame 22 and filter 24. Filter 24 includes holes 27 that permit blood to pass through the filter, while trapping emboli. Vascular filter 20 is collapsed for retrieval by applying a load against ribs 21 that causes collar 25 to slide proximally, thereby closing the vascular filter.

Figure 3:
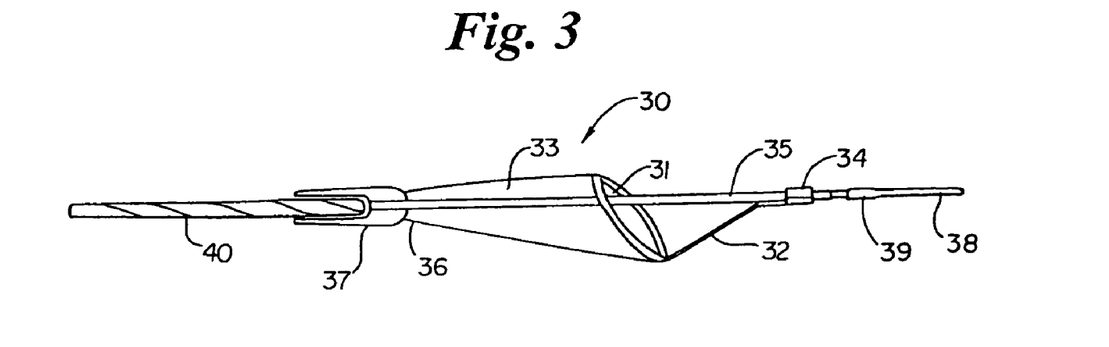
FIG. 3 is a side view of yet another vascular filter suitable for use with the apparatus of the present invention.

Referring now to FIG. 3, another vascular filter suitable for use with the apparatus and methods of the present invention is described. Vascular filter 30 is described in detail in co-pending, commonly assigned U.S. patent application Ser. No. 09/764,774, filed Jan. 16, 2000, and is summarily described here.

Vascular filter 30 preferably includes self-expanding support hoop 31 mounted on suspension strut 32, and supports blood-permeable element 33. Blood-permeable element 33 comprises a biocompatible polymeric material having a multiplicity of pores. Suspension strut 32 is affixed at proximal end 34 to tube 35, and positions support hoop 31 approximately concentric to tube 35 when disposed in a substantially straight length of vessel, but advantageously permits the support hoop to become eccentrically displaced relative to support tube 35 when the filter is deployed in a curved vessel.

Distal end 36 of blood-permeable element 33 is illustratively mounted to nose cone 37, which is in turn mounted to tube 35. Filter 30 is mounted on guidewire 38 between proximal stop 39 and enlarged floppy tip 40 of the guidewire, which functions as a distal stop. Tube 35 permits guidewire 38 to rotate independently of filter 30, thereby permitting floppy tip 40 of the guidewire to be directed within the vessel without causing blood-permeable element 33 to become wrapped around guidewire 38.

The aspiration recovery devices of the present invention are intended to remove emboli proximal to or within a filter sac of a vascular filter, such as those described above in the context of FIGS. 1-3. Additionally, the recovery devices may be used to retrieve the vascular filter. Two families of aspiration recovery devices are provided: a single catheter type and a telescoping dual catheter type. The single catheter type device uses one catheter both to aspirate emboli and retrieve a vascular filter. The telescoping dual catheter type device uses two catheters, with one catheter disposed inside the other, so that the inner catheter is used to aspirate emboli from a vascular filter and the outer catheter is used to retrieve the vascular filter.

Both the single catheter and the telescoping dual catheter types of aspiration recovery devices may be over-the-wire devices or rapid exchange devices. As is well known, in an over-the-wire device, the guidewire is disposed within the entire length of the catheter, whereas in a rapid exchange device the guidewire is disposed only within a short portion at the distal end of the catheter.

Figure 4A:
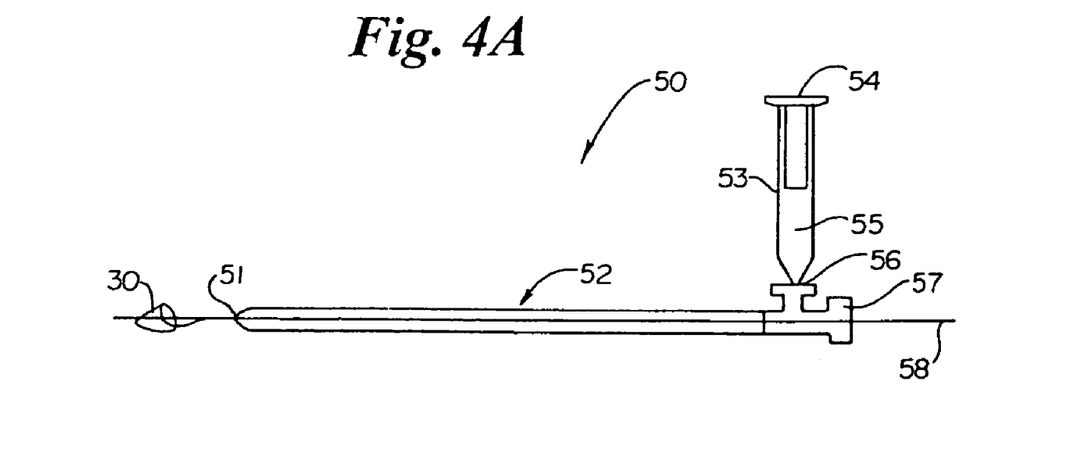
FIG. 4A is a perspective view of an over-the-wire single catheter aspiration recovery device of the present invention.

Referring now to FIG. 4A, an embodiment of an over-the-wire single catheter aspiration recovery device constructed in accordance with the principles of the present invention is described. Aspiration recovery device 50 illustratively includes syringe 53 with plunger 54 and chamber 55. Syringe 53 is coupled to side port 56 of catheter 52. Catheter 52 also includes hemostatic valve 57. Catheter 52 may be used for both aspiration of emboli and retrieval of a vascular filter, for example, vascular filter 30 of FIG. 3.

Syringe 53 may be any existing syringe capable of inducing low pressure in chamber 55 when plunger 54 is retracted, thereby creating a pressure gradient between distal end 51 in the patient's vasculature and chamber 55. This pressure gradient causes fluid and material, specifically blood and emboli, to be aspirated from a region within or proximal to vascular filter 30 to chamber 55 via catheter 52. The amount of blood removed from the patient using syringe 53 preferably is in a range of about 10 ml to 50 ml. The amount of blood aspirated to chamber 55 at the completion of a treatment procedure is generally sufficiently small that no effort need by made to cleanse and reintroduce the blood to the patient's circulatory system. Alternatively, the blood removed from the body may be filtered and reintroduced to the patient, if desired.

While FIG. 4A depicts an over-the-wire single catheter device, syringe 53 also may be used in conjunction with an over-the-wire telescoping dual catheter device, described hereinafter. In addition, while the present invention is illustrated with a syringe as the aspiration inducer, it should be understood that any other suitable device that induces suction may be used, such as a standard suction port available in a hospital operating room.

Figure 4B:
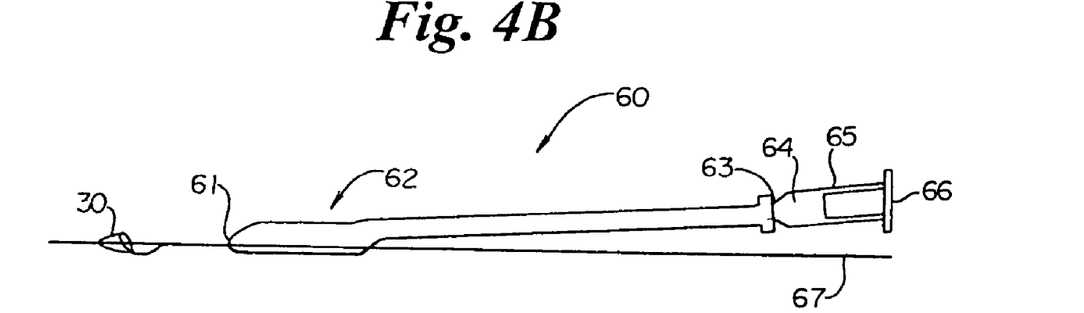
FIG. 4B is a perspective view of a rapid exchange single catheter aspiration recovery device of the present invention.

With respect to FIG. 4B, a rapid exchange embodiment of a single catheter aspiration recovery device is described. Aspiration recovery device 60 includes syringe 65 with plunger 66 and chamber 64 coupled at connection 63 to aspiration catheter 62. Catheter 62 may be used for both aspiration of emboli and retrieval of a vascular filter, such as those described above in FIGS. 1-3.

Syringe 65 preferably is constructed as described above with respect to syringe 53 of FIG. 4A, and is actuated by retracting plunger 66 proximally. When so retracted, fluid and emboli within or proximal to vascular filter 30 are drawn into distal end 61, through catheter 62, and into chamber 64, as described above for the embodiment of FIG. 4A.

Both the rapid exchange and the over-the-wire aspiration recovery devices of the present invention may be used to aspirate emboli liberated from a patient's vessel wall by an interventional device, such as an angioplasty catheter, an atherectomy catheter, an embolectomy catheter, a vascular mapping catheter, stent delivery device or other diagnostic or therapeutic interventional device, from within or proximal to a vascular filter.

Figure 5A:
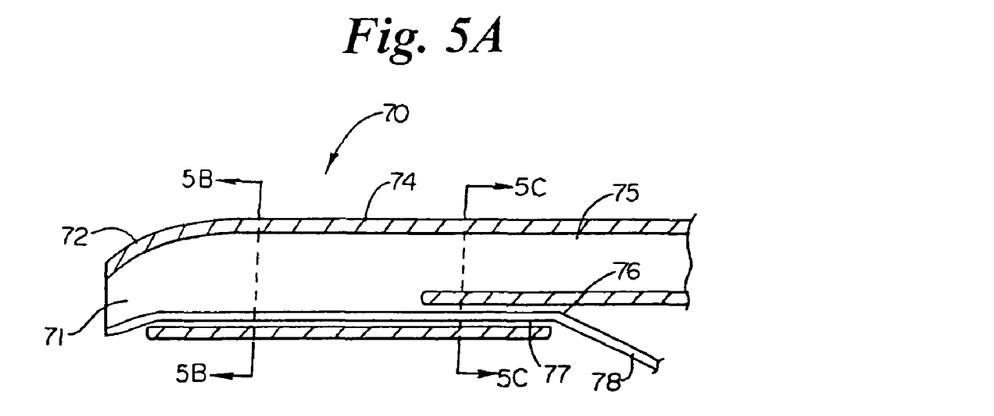
FIG. 5A is a side sectional view of the distal end of a rapid exchange single catheter aspiration recovery device of the present invention.

Referring now to FIG. 5A, a rapid exchange single catheter aspiration recovery device 70 is described. Catheter 74 preferably is constructed of a thin biocompatible material, as described hereinabove, and has sufficient stiffness to permit the catheter to be pushed along a guide wire through curved vasculature within a patient's circulatory system, and will not collapse when the syringe is actuated. The distal end of catheter 74 may include a radiopaque marker or may be entirely radiopaque. Radiopaque is understood to be capable of producing a relatively bright image on a fluoroscopy screen or another imaging technique during a medical procedure. This relatively bright image aids the user in determining the location of the distal end catheter 74. Radiopaque materials may include, but are not limited to, gold, platinum, tungsten alloy, and plastic material loaded with a radiopaque filler.

Figure 5B:
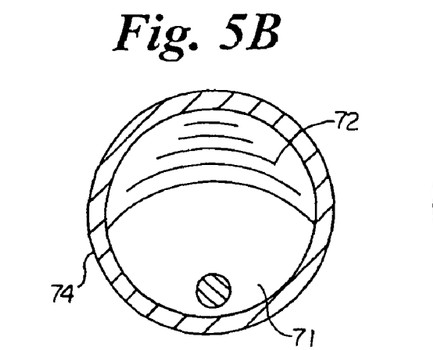
FIGS. 5B-5C are cross sectional views of the aspiration recovery device of FIG. 5A.
Figure 5C:
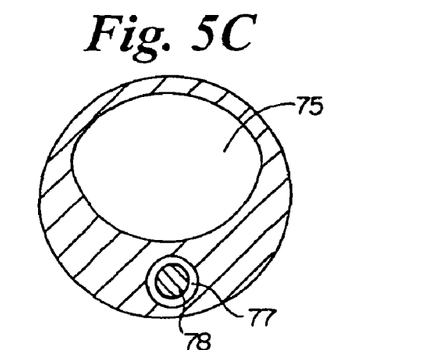
Figure 5D:
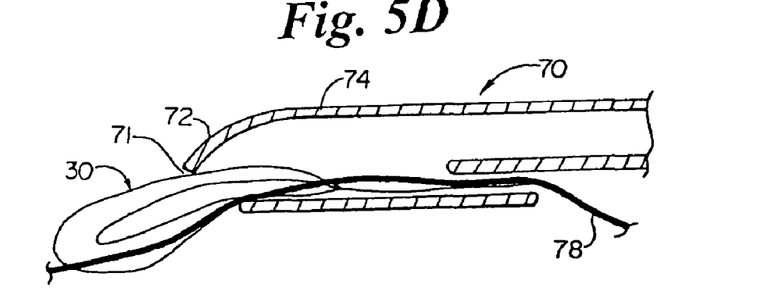
FIG. 5D is a side sectional view of the aspiration recovery device of FIG. 5A and a collapsed vascular filter.

Catheter 74 optionally may include bent tip 72, which has a rounded profile to risk the risk of injury to a patient's vessel, or inadvertently becoming entangled with a stent, as it is advanced toward a treatment area. Opening 71 of tip 72 (see FIG. 5D) provides a rounded profile that enhances trackability. Guidewire 78 enters guidewire lumen 77 proximally through skive 76 and exits catheter 74 through distal opening 71, as illustrated in FIGS. 5B and 5C.

In accordance with the principles of the present invention, catheter 74 is used to aspirate emboli from a location proximal to a vascular filter, using syringe 65 or other suitable suction source. Emboli are aspirated through opening 71 to chamber 64 of syringe 65. Additionally, catheter 74 may be moved slightly in the proximal and distal directions relative to vascular filter 30 to vacuum up emboli disposed proximal to vascular filter 30. Once the aspiration step is completed, catheter 74 then may be advanced toward vascular filter 30 to collapse and retrieve the vascular filter through opening 71. Alternatively, upon completion of the interventional procedure, guidewire 78 and attached vascular filter 30 may be withdrawn proximally until the vascular filter engages and is caused to be collapsed within catheter 74.

Figure 6:
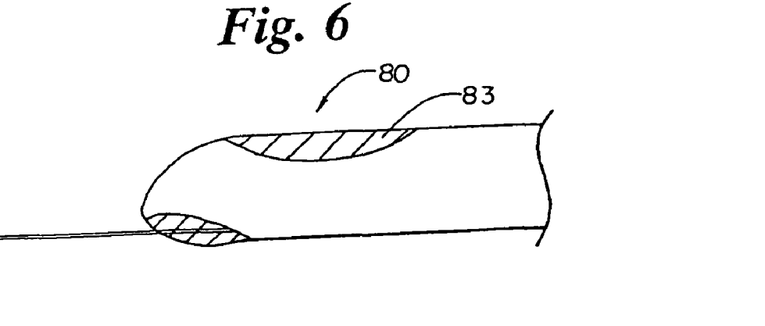
FIG. 6 is a perspective view of the distal end of another embodiment of the rapid exchange single catheter aspiration recovery device of the present invention.

With respect to FIG. 6, the distal end of an alternative embodiment of a rapid exchange single catheter aspiration recovery device of the present invention is described. Device 80 is substantially similar to device 70 of FIG. 5, except that device 80 includes an additional aspiration hole 83 to facilitate aspiration of emboli proximal to a vascular filter. Device 70 may also include a radiopaque marker similar to that described above.

Figure 7:
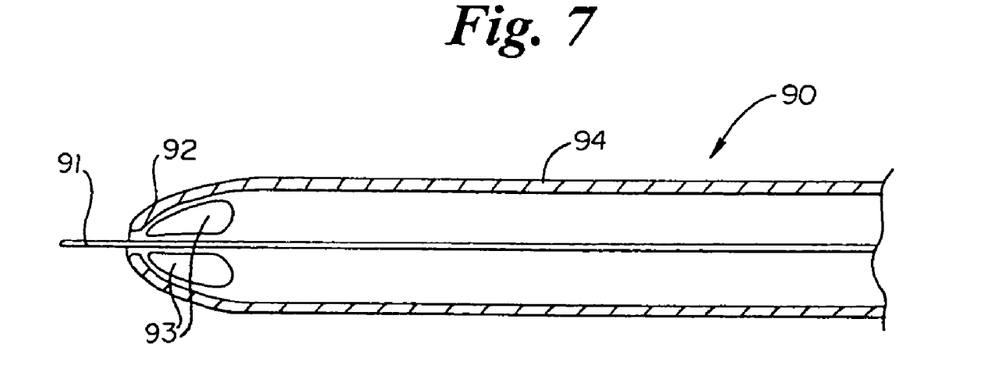
FIG. 7 is a side sectional view of the distal end of an over-the-wire single catheter aspiration recovery device of the present invention.
Figure 8A:
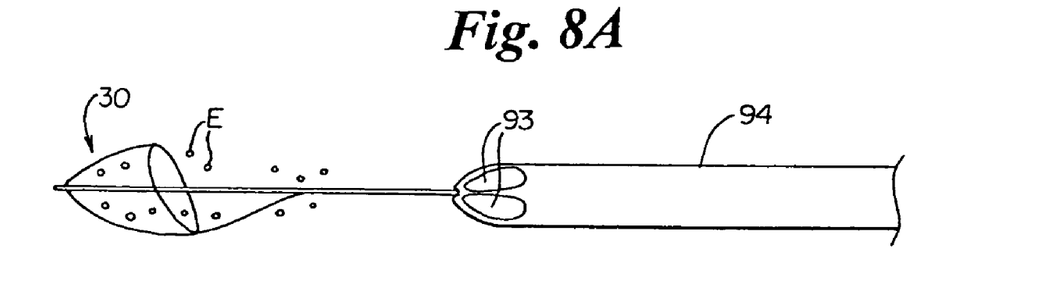
FIGS. 8A-8B are perspective views depicting a method of aspirating emboli and recovering a vascular filter using the aspiration recovery device of FIG. 7.
Figure 8B:
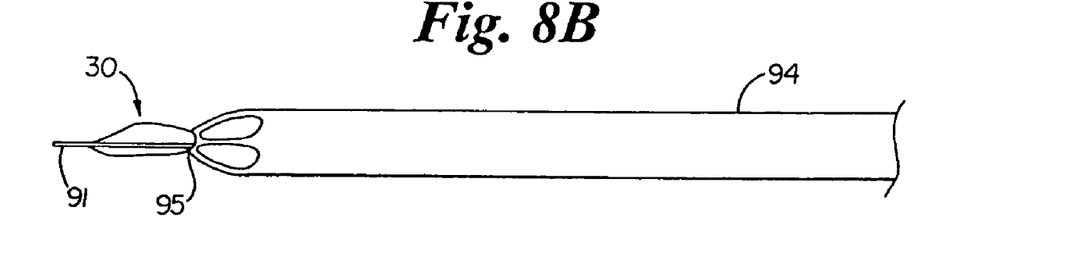

Referring to FIGS. 7 and 8, the distal end of an over-the-wire single catheter aspiration recovery device 90 is now described. Preferably, catheter 94 is constructed as described hereinabove, and may include a radiopaque marker or may be entirely radiopaque to permit the viewing of the catheter using a fluoroscope. Catheter 94 includes tapered tip 92, wherein the leading edges are rounded to reduce the risk of vessel injury or stent entanglement.

Catheter 94 may be used to aspirate emboli from a location proximal to vascular filter 30 using syringe 53 as described above with respect to FIG. 4A. Emboli E that are both proximal to and within vascular filter 30 may travel proximally and enter aspiration holes 93 of catheter 94 when suction is induced through the catheter, for example, by actuating syringe 53 (see FIG. 4A). After the aspiration step is completed, catheter 94 may be advanced distally toward vascular filter 30 to collapse and retrieve the vascular filter in opening 95, or alternatively, guidewire 91 and attached vascular filter 30 may be withdrawn proximally to retrieve the vascular filter into opening 95 of catheter 94.

Figure 9:
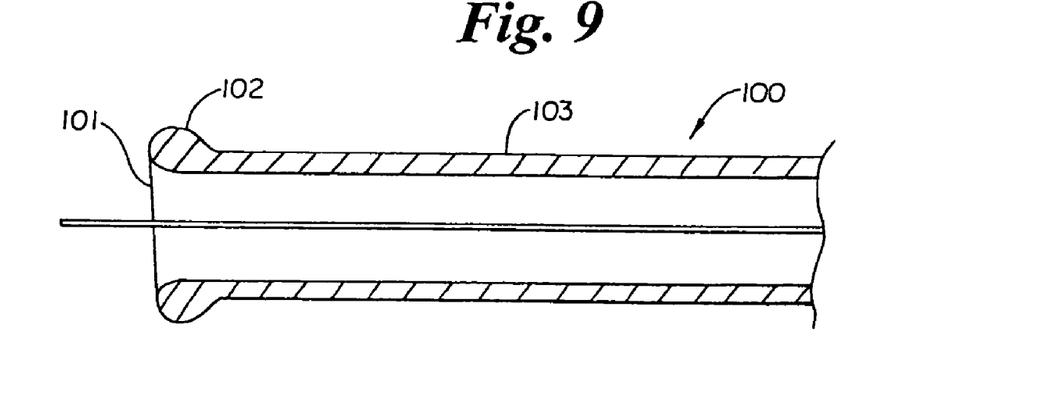
FIG. 9 is a side sectional view of the distal end of another embodiment of the over-the-wire single catheter aspiration recovery device of the present invention.

With respect to FIG. 9, device 100 is substantially similar to device 90 of FIGS. 7 and 8, except that device 100 includes bump tip 102 with opening 101 to facilitate aspiration of emboli from a location proximal to a vascular filter and to collapse the vascular filter. Tip 102 is rounded to reduce the risk of vessel injury or stent entanglement.

With reference to FIGS. 10A-10D, a rapid exchange telescoping catheter aspiration recovery device 110 is described. Device 110 includes aspiration catheter 112 disposed within a lumen of retrieval catheter 113. Preferably, aspiration catheter 112 and retrieval catheter 113 are constructed as described hereinabove for previous catheter embodiments and may include a radiopaque marker.

Distal end 114 of aspiration catheter 112 is configured to reduce the risk of becoming entangled with a stent disposed within a patient's vessel. Distal end 114 includes rounded edge 117 disposed at angle 116 to facilitate movement through the vessel, and to improve maneuverability of catheter 112 by creating a leading edge to track through the vessel. Angle 116 preferably is less than 90-degrees, resulting in oblique opening 115 of distal end 114.

Figure 10A:
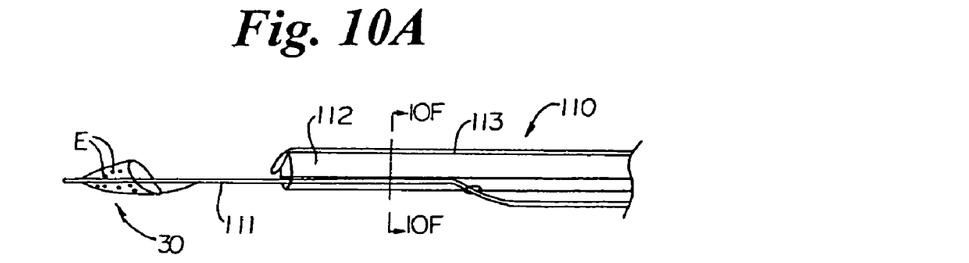
FIGS. 10A-10D are perspective views depicting a method of aspirating emboli and recovering a vascular filter using a rapid exchange telescoping catheter aspiration recovery device of the present invention.

In FIGS. 10A-10D, a method for aspirating emboli and retrieving a vascular filter is illustrated. FIG. 10A illustrates a step of a treatment procedure, wherein vascular filter 30 is disposed at a distal end of guidewire 111 followed by aspiration catheter 112 and retrieval catheter 113. FIG. 10F depicts guidewire 111 disposed within a guide wire lumen of retrieval catheter 113, and externally to aspiration catheter 112. At the conclusion of an interventional procedure, the interventional device is removed and aspiration recovery catheter 110 then is advanced along guidewire 111 to a position just proximal of vascular filter 30.

Figure 10B:
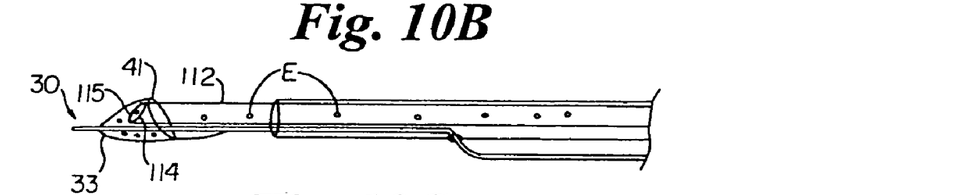

As depicted in FIG. 10B, aspiration catheter 112 is advanced distally through mouth 41 and into blood-permeable element 33 of vascular filter 30. Suction is then applied to the proximal end of catheter 112 to aspirate emboli E from within blood-permeable element 33 into opening 115, and through aspiration catheter 112. Aspiration catheter 112 also may be moved in small distances back and forth within blood-permeable element 33 to permit distal end 114 to unburden vascular filter 30.

Figure 10C:
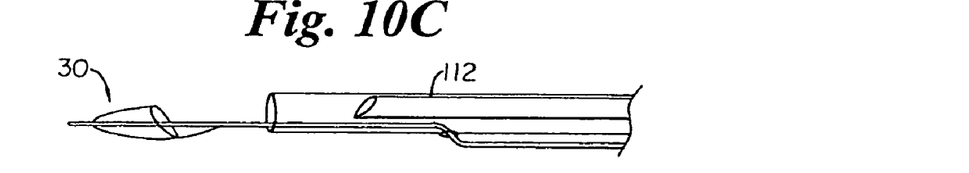
Figure 10D:
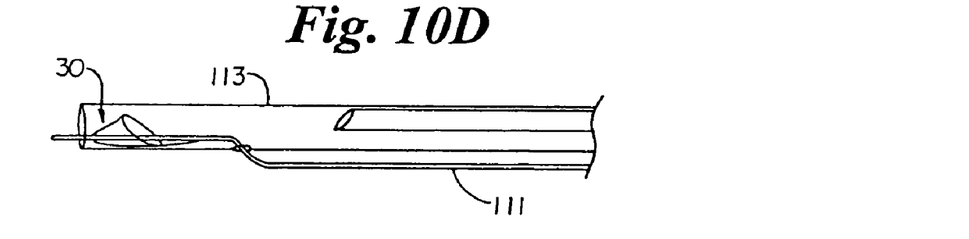
Figure 10E:
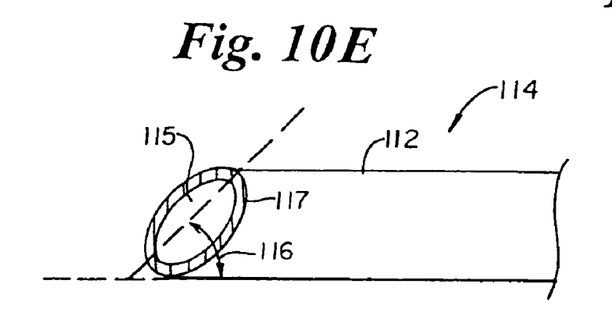
FIG. 10E is a perspective view of the distal end of the aspiration recovery device of FIGS. 10A-10D.
Figure 10F:
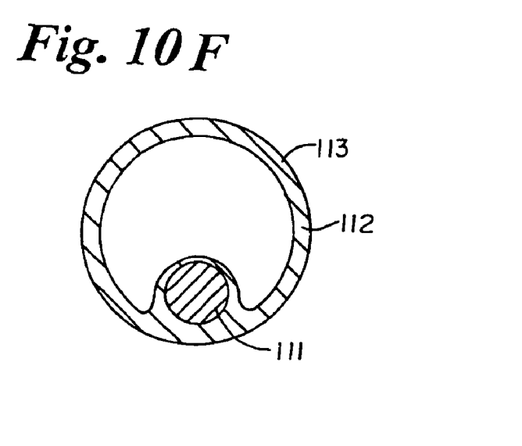
FIG. 10F is a cross sectional view of the aspiration recovery device of FIGS. 10A-10D.

As shown in FIG. 10C, aspiration catheter 112 then is retracted proximally into retrieval catheter 113. In FIG. 10D, retrieval catheter 113 then is advanced distally to encapsulate vascular filter 30. Catheters 112 and 113, guidewire 111 and vascular filter 30 may then be removed from the patient's vasculature. Alternatively, guidewire 111 and attached vascular filter 30 may be withdrawn proximally into retrieval catheter 113.

Figure 11A:
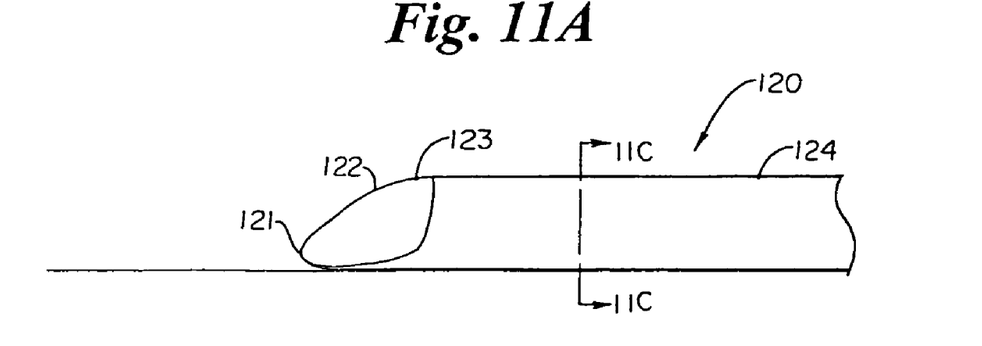
FIGS. 11A-11B are perspective views of the distal end of another embodiment of the rapid exchange telescoping catheter aspiration recovery device of the present invention.
Figure 11B:
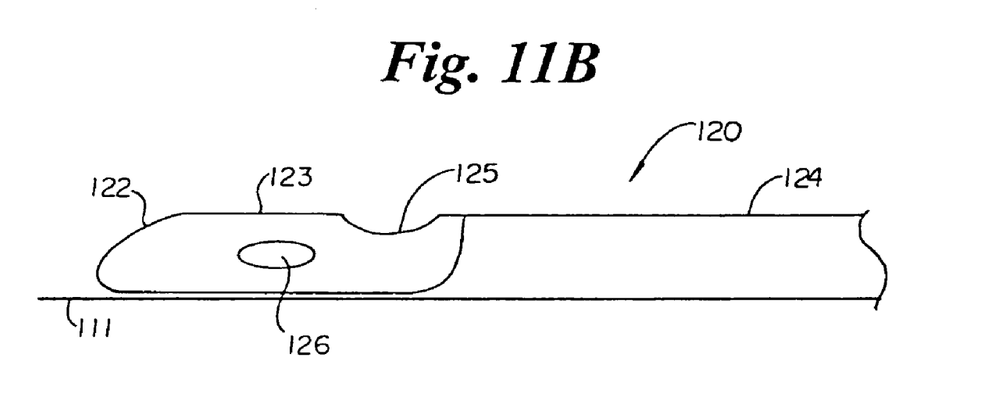
Figure 11C:
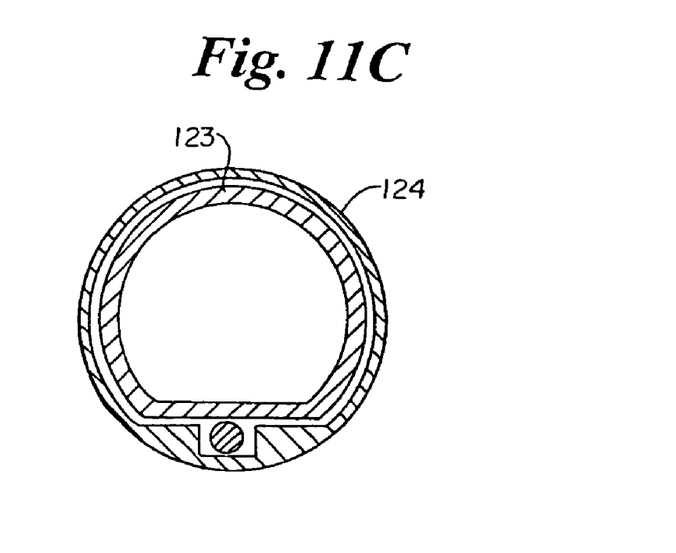
FIG. 11C is a cross sectional view of the aspiration recovery device of FIGS. 11A-11B.

With respect to FIGS. 11A-11C, another embodiment of the rapid exchange telescoping catheter aspiration recovery device of the present invention is described. Device 120 is substantially similar to device 110 of FIG. 10, except that device 120 also includes nose cone 122, one or more aspiration holes 126, aspiration hole 125, and inner catheter 123 is keyed to outer catheter 124 (see FIG. 11C).

Nose cone 122 facilitates tracking through a patient's vessel, and preferably includes rounded tip 121, which reduces the risk of vessel injury or stent entanglement. Advancing aspiration catheter 123 from within retrieval catheter 124 toward a vascular filter, such as vascular filter 30, exposes aspiration holes 125 and 126, as shown in FIG. 11B, which as otherwise covered by retrieval catheter 124 as device 120 travels toward vascular filter 30. This arrangement reduces the risk that aspiration holes 125 and 126 will become entangled with a stent strut as device 120 is advanced toward a treatment site along guidewire 111.

As shown in FIG. 11C, catheter 123 is keyed within catheter 124 to maintain relative alignment of the catheters. This ensures that the aspiration catheter is at a proper orientation when entering a vascular filter, such as vascular filter 30.

Figure 12:
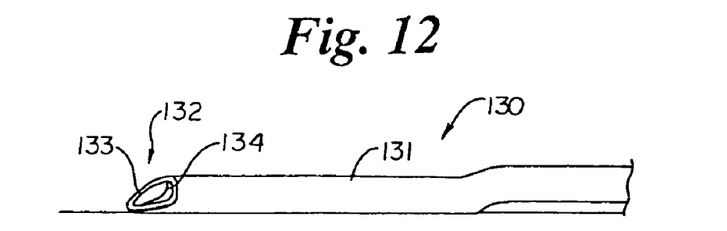
FIG. 12 is a perspective view of the distal end of yet another embodiment of the rapid exchange telescoping catheter aspiration recovery device of the present invention.
Figure 13A:
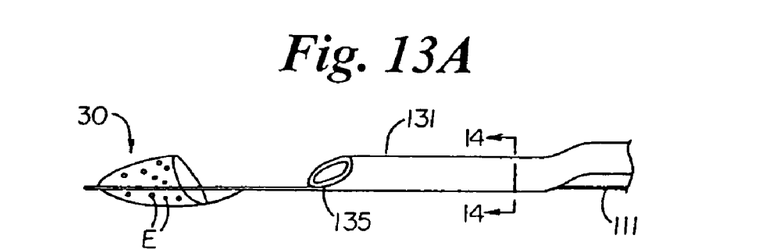
FIGS. 13A-13C are perspective views depicting a method of aspirating emobli and recovering a vascular filter using the aspiration recovery device of FIG. 12.
Figure 13B:
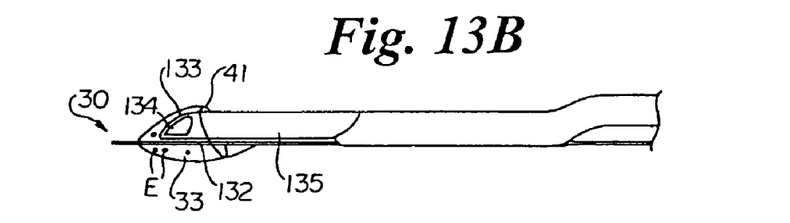
Figure 13C:
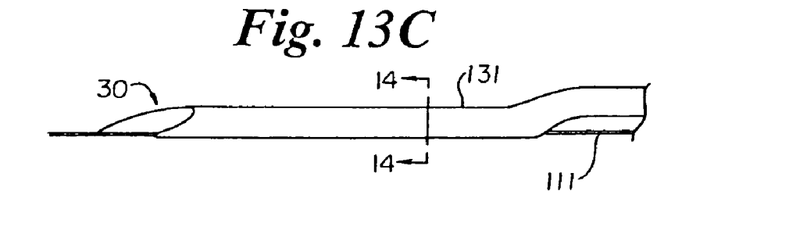
Figure 14:
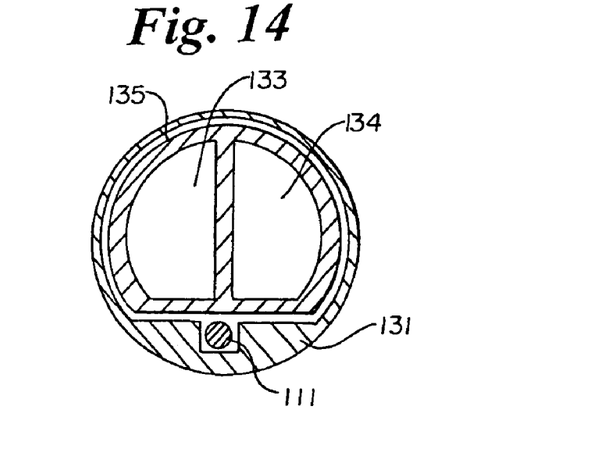
FIG. 14 is a frontal view of the aspiration recovery device of FIG. 12.

FIGS. 12-14 show yet another embodiment of the rapid exchange telescoping catheter aspiration recovery device of the present invention. Device 130 is substantially similar to device 120 of FIG. 11, except that device 130 includes distal end 132 with aspiration holes 133 and 134, rather than a nose cone and aspiration holes that are hidden by a retrieval catheter.

In FIG. 13A, vascular filter 30 is disposed at a distal end of guidewire 111 followed by aspiration catheter 135 and retrieval catheter 131. This arrangement may be used to aspirate emboli E from vascular filter 30 following a treatment procedure such as angioplasty involving an interventional device such as an angioplasty catheter (not shown) and vascular filter 30.

In FIG. 13B, aspiration catheter 135 is moved distally through mouth 41 and into blood-permeable element 33 of vascular filter 30, and suction is drawn on the proximal end of aspiration catheter 133 to aspirate emboli E from within blood-permeable element 33. In FIG. 13C, aspiration catheter 135 then is retracted proximally to exit vascular filter 30, and retrieval catheter 131 is advanced distally to retrieve vascular filter 30. Alternatively, guidewire 111 and attached vascular filter 30 may be withdrawn proximally until the vascular filter is retrieved within catheter 131.

Figure 15:
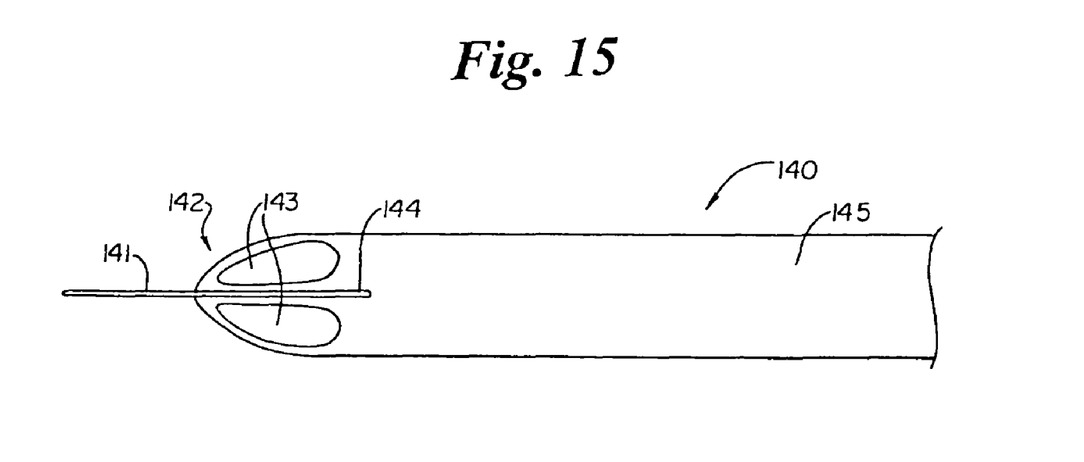
FIG. 15 is a perspective view of the distal end of an over-the-wire telescoping catheter aspiration recovery device of the present invention.
Figure 16A:
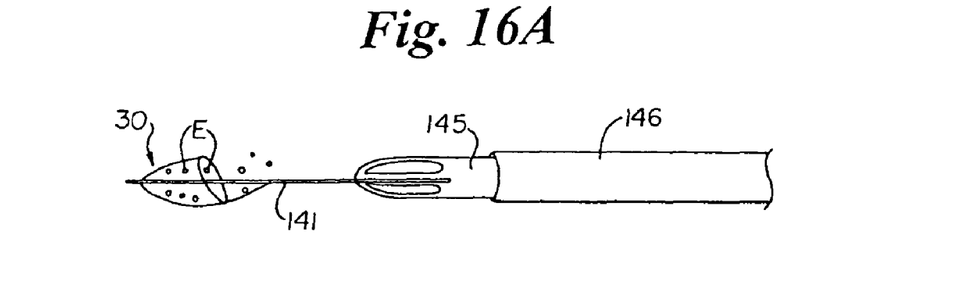
FIGS. 16A-16C are perspective views depicting a method of aspirating emboli and recovering a vascular filter using the aspiration recovery device of FIG. 15.
Figure 16B:
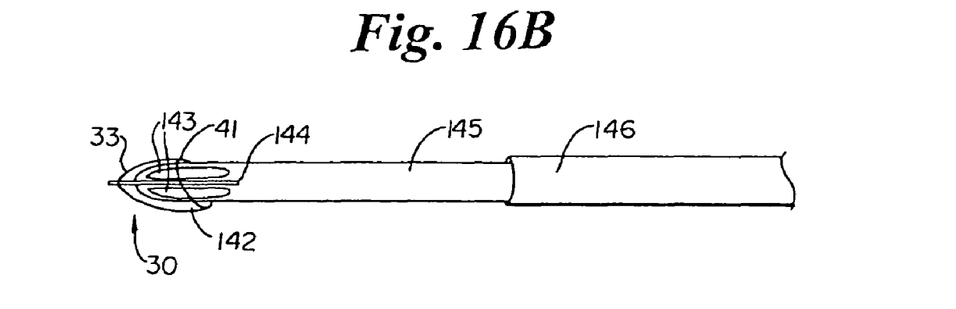
Figure 16C:
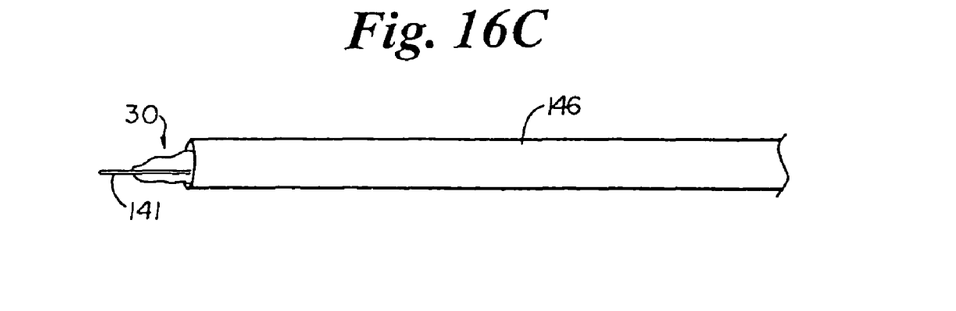

FIGS. 15-16C show over-the-wire telescoping catheter aspiration recovery device 140. Device 140 includes aspiration catheter 145 with aspiration holes 143 and slit 144 and retrieval catheter 146. Preferably, aspiration catheter 145 and retrieval catheter 146 are constructed as described hereinabove, and are used in a method similar to that of catheters 112 and 113 of FIG. 10.

The present invention describes a method of aspirating emboli from a filter sac of a vascular filter prior to retrieval. However, a similar method may be used to aspirate emboli from the filter sac of the vascular filter during a procedure (not shown), for example, in the event that the sac of the vascular filter fills to capacity during a treatment procedure. Additionally, the present invention may be used to aspirate emboli from around a stent which may be in place within a patient's vessel.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for filtering and aspirating emboli from a vessel comprising:
    a guidewire;
    a vascular filter mounted on the guidewire, the vascular filter including a blood-permeable element, the vascular filter causing emboli to become deposited in the vessel in the vicinity of the vascular filter; and
    a first catheter having proximal and distal ends, proximal and distal openings, and a lumen defined by a catheter wall extending between the proximal and distal openings, the distal end of the first catheter has a rounded end with the distal opening off-center such that, when viewed in a cross-section that extends along a central longitudinal axis of the lumen, the catheter wall extends in a generally straight fashion towards the proximal end from the distal opening on a first side and, on a second side opposite the first side, has a first portion nearest the distal opening that is curved in a concave fashion towards the lumen and a second portion extending proximally from the first portion in a generally straight fashion towards the proximal end;
    wherein the guidewire passes through the distal opening, is at least partially disposed within the lumen, and passes through a port disposed in the catheter wall proximal of the distal end and distal of the proximal end;
    wherein the first catheter is adapted to be advanced along the guidewire to a location in the vessel in the vicinity of the vascular filter to aspirate emboli;
    wherein the concave curve of the first portion at least partially defines the distal opening.

2. The apparatus of claim 1, wherein the distal end of the first catheter is dimensioned to permit the distal opening to enter the blood-permeable element.

3. The apparatus of claim 1, wherein the distal end of the first catheter includes one or more aspiration holes disposed proximal of the distal opening.

4. The apparatus of claim 1, wherein the first catheter comprises a rapid exchange device.

5. The apparatus of claim 1, further comprising a second catheter having proximal and distal ends, proximal and distal openings, and a lumen extending between the proximal and distal openings, the lumen of the second catheter dimensioned to accept the first catheter therein.

6. The apparatus of claim 5, wherein the first catheter includes one or more aspiration holes disposed proximal of the distal opening and the second catheter selectively occludes the one or more aspiration holes.

7. The apparatus of claim 5, wherein the distal opening of the second catheter is dimensioned so that the vascular filter may be at least partially retracted in the lumen of the second catheter.

8. Apparatus for filtering and aspirating emboli from a vessel comprising:
   a guidewire;
   a vascular filter mounted on the guidewire, the vascular filter including a blood-permeable element, the vascular filter causing emboli to become deposited in the vessel in the vicinity of the vascular filter; and
   a first catheter having proximal and distal ends, proximal and distal openings, and a lumen defined by a catheter wall extending between the proximal and distal openings, the distal end of the first catheter has a rounded end with the distal opening off-center such that, when viewed in a cross-section that extends along a central longitudinal axis of the lumen, the catheter wall extends in a generally straight fashion towards the proximal end from the distal opening on a first side and, on a second side opposite the first side, has a first portion nearest the distal opening that is curved in a concave fashion towards the lumen and a second portion extending proximally from the first portion in a generally straight fashion towards the proximal end;
   wherein the guidewire passes through the distal opening, is at least partially disposed within the lumen, and passes through a port disposed in the catheter wall proximal of the distal end and distal of the proximal end;
   wherein the first catheter is adapted to be advanced along the guidewire to a location in the vessel in the vicinity of the vascular filter to aspirate emboli;
   wherein the concave curve of the first portion at least partially defines the distal opening;
   wherein the distal opening of the first catheter is adapted to accommodate at least a portion of the vascular filter within the lumen of the first catheter.

9. The apparatus of claim 8, wherein the distal end of the first catheter is dimensioned to permit the distal opening to enter the blood-permeable element.

10. The apparatus of claim 8, wherein the distal end of the first catheter includes one or more aspiration holes disposed proximal of the distal opening.

11. The apparatus of claim 8, wherein the first catheter comprises a rapid exchange device.

12. The apparatus of claim 8, further comprising a second catheter having proximal and distal ends, proximal and distal openings, and a lumen extending between the proximal and distal openings, the lumen of the second catheter dimensioned to accept the first catheter therein.

13. The apparatus of claim 12, wherein the first catheter includes one or more aspiration holes disposed proximal of the distal opening and the second catheter selectively occludes the one or more aspiration holes.

14. The apparatus of claim 12, wherein the distal opening of the second catheter is dimensioned so that the vascular filter may be at least partially retracted in the lumen of the second catheter.

* * * * *